United States Patent
Wagner (10) Patent No.: US 9,566,427 B2
(45) Date of Patent: Feb. 14, 2017

(54) FRAME WITH A NOSEPIECE AND AN ELECTRODE HOLDER FOR AN ELECTRODE FOR ELECTROSTIMULATION OF THE EYE

(71) Applicant: OKUVISION GMBH, Reutlingen (DE)

(72) Inventor: Holger Wagner, St. Johann (DE)

(73) Assignee: OKUVISION GMBH, Reutlingen (DE)

(*) Notice: Subject to any disclaimer, the term of this patent is extended or adjusted under 35 U.S.C. 154(b) by 117 days.

(21) Appl. No.: 14/361,283

(22) PCT Filed: Nov. 20, 2012

(86) PCT No.: PCT/EP2012/073085
§ 371 (c)(1),
(2) Date: May 28, 2014

(87) PCT Pub. No.: WO2013/079357
PCT Pub. Date: Jun. 6, 2013

(65) Prior Publication Data
US 2014/0324147 A1    Oct. 30, 2014

(30) Foreign Application Priority Data
Nov. 29, 2011  (DE) .......... 10 2011 055 844

(51) Int. Cl.
- *A61N 1/36* (2006.01)
- *A61N 1/04* (2006.01)
- *G02C 11/00* (2006.01)

(52) U.S. Cl.
CPC ........... *A61N 1/0472* (2013.01); *A61N 1/0456* (2013.01); *A61N 1/36046* (2013.01); *G02C 11/00* (2013.01)

(58) Field of Classification Search
CPC . A61N 1/0472; A61N 1/0476; A61N 1/36046
See application file for complete search history.

(56) References Cited

U.S. PATENT DOCUMENTS

| 3,376,870 A | 4/1968 | Yamamoto et al. |
| 4,331,163 A | 5/1982 | Nomura |
| (Continued) | | |

FOREIGN PATENT DOCUMENTS

| DE | 102010027201 | 7/2011 |
| WO | WO-2011/086150 | 7/2011 |

OTHER PUBLICATIONS

International Preliminary Report on Patentability and Written Opinion for PCT/EP2012/073085, dated Jun. 3, 2014, 6 pages.
(Continued)

*Primary Examiner* — Christopher D Koharski
*Assistant Examiner* — Natasha Patel
(74) *Attorney, Agent, or Firm* — Morrison & Foerster LLP (57) ABSTRACT

A stimulation electrode arrangement for a device (10) for electrostimulation of the eye is described, the device (10) having a spectacles-like frame (11) with a nosepiece (12), an arrangement, connected to the nosepiece (12), for holding the frame (11) on the head of the patient, and at least one electrode holder (24, 25), arranged on the nosepiece (12) in adjustable fashion, for the wire-shaped stimulation electrode (26, 27). The stimulation electrode arrangement comprises an electrode carrier, which can be attached to the electrode holder (24, 25) in detachable fashion and on which the stimulation electrode (26, 27) is arranged.

18 Claims, 5 Drawing Sheets

(56) References Cited

U.S. PATENT DOCUMENTS

| | | | | |
|---|---|---|---|---|
| 5,154,174 A | * | 10/1992 | Hawlina | A61B 5/0496 |
| | | | | 600/383 |
| 5,360,438 A | * | 11/1994 | Fisher | A61N 1/36014 |
| | | | | 607/141 |
| 5,527,357 A | | 6/1996 | Springer, Jr. | |
| 8,639,345 B2 | | 1/2014 | Eipper et al. | |
| 2009/0312817 A1 | * | 12/2009 | Hogle | A61B 5/0492 |
| | | | | 607/54 |

OTHER PUBLICATIONS

International Search Report for PCT/EP2012/073085, mailed Jan. 7, 2013, 4 pages.

\* cited by examiner

FRAME WITH A NOSEPIECE AND AN ELECTRODE HOLDER FOR AN ELECTRODE FOR ELECTROSTIMULATION OF THE EYE

CROSS-REFERENCE TO RELATED APPLICATIONS

This application is the national phase of PCT application PCT/EP2012/073085 having an international filing date of Nov. 20, 2012, which claims priority to German Patent Application No. 10 2011 055 844.6, filed on Nov. 29, 2011. The entire contents of the above-listed applications are incorporated herein by this reference in their entireties.

The present invention relates to a stimulation electrode arrangement for a device for electrostimulation of the eye, the device having a spectacles-like frame with a nosepiece, an arrangement, connected to the nosepiece, for holding the frame on the head of the patient, and at least one electrode holder, arranged on the nosepiece in adjustable fashion, for a wire-shaped stimulation electrode.

The present invention furthermore relates to an electrode holder for such a stimulation electrode arrangement and to a corresponding device for electrostimulation of the eye.

Such stimulation electrodes, electrode holders and devices are known from WO 2011/086150 A2.

The known stimulation electrode is a wire-shaped electrode which is attached to the spectacles-like frame. When the frame is arranged on the head of a patient, the flexible wire electrode comes into contact with the cornea of the eye. A counter electrode is either provided on the frame or is attached separately on the forehead of the head.

The wire electrode and the counter electrode can be used to route a pulse-like electrical stimulation signal into the eye, leading to a stimulation current flowing via the cornea into the eye.

The known device and other devices are used to route electrical stimulation signals into the eye because it was found that this can stabilize or even improve certain forms of retinopathia pigmentosa and other eye diseases.

Retinal degeneration is a significant cause of blindness in industrialized countries. Various trials provide indications that low electrical currents which flow through the retina can delay the onset of genetic, age-related or sudden degeneration of the retina.

This opens up the possibility of being able to delay the gradual loss of sight by means of regular, that is to say e.g. daily or weekly, electrical stimulation of the eye in order thus to maintain parts of the vision for longer in affected patients, or even restore parts of the vision.

Expediently, this treatment should be carried out by the patient himself and at home. In doing so, in the extreme case, the assumption must be made that the patient is practically blind. The result of this is that there are significant demands on the device and the stimulation electrode mentioned at the outset.

This is because the wire-shaped stimulation electrode must be replaced after every use, or at least very frequently. On the one hand, the wire-shaped stimulation electrode is a very thin electrode, which can break in the case of improper or even frequent use.

On the other hand, considerations in respect of hygiene may make it necessary to replace the stimulation electrode after each use.

WO 2011/086150 A2, mentioned at the outset, describes three different embodiments for these applications.

In a first embodiment, the device for electrostimulation of the eye is designed in the style of spectacles, with spiral electrode holders, which extend towards the eye, thereby being provided on the frame which is usually provided for the lenses. Two such electrode holders are provided for each eye, and so a wire electrode needs to be connected to the two inner ends of these flexible electrode holders in order to come into contact with the cornea when the spectacles are put on.

In a second embodiment, a facemask is shown, which is fitted over an area to parts of the face of the patient. Eye openings, on which pushbuttons are provided, into which the wire-shaped stimulation electrodes are hooked, are provided in this facemask.

In a third embodiment, a type of "shooting spectacles" is shown, in which the spectacles-like frame comprises a nose clip and two eye brackets coming off the former, which eye brackets are in turn connected to foldable earpieces.

Each two electrode holders are attached to the eye brackets; said electrode holders can be adjusted along the eye bracket and perpendicular to the eye bracket, i.e. in all three directions.

On their inner free ends, the electrode holders are respectively connected to ears, into which the wire-shaped stimulation electrode is introduced. The stimulation electrode is attached with its first end to the nose-side electrode holder and is then routed through an ear to the temple-side electrode holder. At its second end, the stimulation electrode is weighed down by a weight such that the stimulation electrode is pretensioned in this manner.

A person skilled in the art fits this frame to the head of the patient such that, when such spectacles which are equipped with one or two stimulation electrodes are put on, the stimulation electrode automatically rests against the eye.

Whereas a person skilled in the art sets the geometric conditions of the frame on one occasion, the patient should subsequently use the device at home in order to subject his eyes to regular electrical stimulation.

However, hooking the stimulation electrode into the ears or onto the electrode holder, which is required for this, is found to be extremely difficult for patients with visual impairments. In part, the thin electrode thread is not recognized by the patients or said electrode thread can slide out of the electrode holders when the spectacles frame is put on.

In order to prevent this, the stimulation electrode must be wound a number of times around the holder at the nose-side electrode holder. This requires much dexterity because, firstly, the thread is rigid and, secondly, the patients have to resort to their sense of touch as a result of their visual impairment.

In view of the above, the object of the present invention is to improve a stimulation electrode arrangement of the type mentioned at the outset such that, while having a cost-effective design suitable for mass production, it is easy to handle such that even visually impaired patients can mount it onto the device without problems.

According to the invention, this object is achieved with the stimulation electrode arrangement mentioned at the outset in that it comprises an electrode carrier, which can be attached to the electrode holder in detachable fashion and on which the stimulation electrode is arranged.

Here, the inventor of the present application has not gone down the path of equipping the stimulation electrode itself with additional ears or hooks; rather the stimulation electrode is now supplied together with an electrode carrier, on which it is arranged in non-detachable fashion.

The wire-shaped stimulation electrode and the electrode carrier therefore, as a stimulation electrode arrangement, form one economic unit, which is made available in pre-assembled form as a disposable article.

Then the patient only needs to grip the stimulation electrode arrangement by the electrode carrier, which is much more massive than the thin stimulation electrode, and attach this electrode carrier in the electrode holder which is already present and adjusted on the device.

Since the electrode carrier has greater mass and greater dimensions than the stimulation electrode itself, visually impaired or even blind patients can feel the electrode carrier and insert it, in the correct position, into the electrode holder.

The object underlying the invention is thereby achieved in its entirety.

Here, it is preferable for the stimulation electrode to be a DTL-like electrode, preferably an electrode made of a wire of noble metal or a special steel alloy or a polymer thread with a metallic coating.

Furthermore, it is preferable for the stimulation electrode to be, on the first end thereof, connected to the electrode carrier in electrically conductive fashion, with, preferably, the electrode carrier being provided with an electrical plug-in contact for the electrode holder, and the first end of the stimulation electrode being electrically connected to the plug-in contact.

An advantage of this measure is that the electrical contacting of the stimulation electrode also takes place at the same time as when the electrode carrier is mechanically attached to the electrode holder. Thus, the patient need not take any further measures so that the stimulation electrode, which was mechanically attached to the electrode holder with the aid of the electrode carrier, can be contacted electrically.

Here, it is furthermore preferable for the stimulation electrode to be routed through at least one passage opening on the electrode carrier and provided with a weight at the second end thereof.

As a result of using weights, putting a newly inserted stimulation electrode against the eye is made so much easier that this can also be undertaken by a severely visually impaired or blind patient.

Since the electrode thread which is strained by the weights is routed through a passage opening on the electrode carrier, the stimulation electrode is, as it were, mounted in flexible fashion such that it matches the contour of the eye without problems.

Here, it is preferable for the electrode carrier to be formed as a U-shaped bracket with two arms, with respectively one passage opening, through which the stimulation electrode runs, being arranged on the first and the second arms and with the plug-in contact being arranged on the second arm.

An advantage of this measure is that use is made of an electrode carrier with a simple design which, particularly if it is made as an injection-moulded part, can be produced in a simple and cost-effective fashion, even in small quantities. As a result of the low production costs, the economical unit of stimulation electrode and electrode carrier can also be used as a disposable article, which, moreover, can easily be sterilized.

Here, it is preferable for the first arm to be longer, preferably 4 to 20 mm longer, than the second arm.

This measure, too, is advantageous in terms of cost factors and in terms of handling factors. The electrode carrier is shorter on the arm on which the stimulation electrode is mechanically fixed and electrically contacted than on the other arm where the stimulation electrode passes through the through passage and then is held under tension by the weight.

This stimulation electrode with electrode carrier can now be used for both the right eye and the left eye, with the shorter arm of the electrode carrier being aligned nose side in each case.

If the associated electrode holder for the left and right eye is now likewise embodied with arms of different length, the visually impaired or blind patient also can identify on the basis of the different-length arms of the electrode carrier with which alignment the electrode carrier needs to be put on the electrode holder.

If provision in this case is additionally made for a latching device between the electrode carrier and the electrode holder, which latching device only latches in an audible and tactile manner if the electrode carrier is pushed onto the electrode holder with the correct alignment, the result of this is an additional check for the patient as to whether the stimulation electrode has been mounted correctly.

In view of the above, it is preferred if an on the U-shaped bracket an outwardly open groove is provided for receiving the electrode holder, which electrode holder has a U-shaped wire body.

An advantage of this measure is that the handling is possible in a very simple manner. The patient merely needs to insert the U-shaped bracket into the U-shaped wire body and, while doing so, take care that the electrode carrier is aligned such that the longer arm thereof comes to rest on the longer leg of the wire body.

Here, the outwardly open groove only completely latches onto the wire body when this alignment was selected correctly. Otherwise, a gap remains between bracket and wire body, which can be felt without problems by means of the fingers. The patient can then pull the electrode carrier off the electrode holder again, rotate it by 180° and put it back on again.

Here, it is preferable for respectively one blind-hole bore, for holding respectively one leg of the wire body and running approximately perpendicular to the respective passage opening, to be provided on the first and the second arms.

This measure is also preferred in terms of handling factors since the bracket is not only inserted into the wire body, but rather the wire body reaches into the blind-hole bore with the free ends of its legs, and so the electrode carrier is attached very securely to the electrode holder.

Here, it is furthermore preferable if, in the second arm, the passage opening runs through the blind-hole bore in which a metal sleeve is situated which mechanically fixes the first end of the stimulation electrode in the passage opening and serves as plug-in contact for holding and electrically contacting a leg of the wire body.

This measure has right a number of advantages. First of all, it simplifies the production of stimulation electrode and electrode carrier, and the assembly thereof to form the stimulation electrode arrangement according to the invention, and so the production costs overall are low.

The stimulation electrode merely needs to be pushed through the passage opening in the longer arm and then pushed through the passage opening in the shorter arm. Then the metal sleeve is pushed into the blind-hole bore of the shorter arm, said metal sleeve in the process wedging the free end of the stimulation electrode in the passage bore. As a result, there simultaneously is secure contacting of the stimulation electrode via the metal sleeve, into which in turn a leg of the wire body of the electrode holder is then inserted such that secure and simple contacting also takes place at said location.

A further advantage consists of the fact that the stimulation electrode and the electrode holder contact one another in an electrically insulating electrode carrier, and so the stimulation electrode cannot form a short circuit with other electrical parts of the device or with the skin.

Here, it is preferable for the blind-hole bore in the second arm to be provided with a longitudinal slit in the wall thereof and with a collar surrounding the opening thereof.

This measure is also advantageous in terms of production factors because the blind-hole bore can spring open as a result of the longitudinal slit when the metal sleeve is pushed into the opening. As soon as the metal sleeve is situated completely within the blind-hole bore, the latter springs back such that the collar thereof securely holds the metal sleeve in the blind-hole bore. As a result, this simultaneously ensures a mechanical hold of the first end of the stimulation electrode and secure electrical contacting.

In view of the above, the present invention also relates to an electrode holder for such a stimulation electrode arrangement, which electrode holder has a preferably U-shaped wire body for plugging on the electrode carrier and a holding pin, by means of which it can be attached to the nosepiece in adjustable fashion. The electrode holder is preferably made of electrically conductive material, more preferably of German silver.

Just like the electrode carriers, such electrode holders can be made with different dimensions such that they can be optimally selected for different physiognomic conditions in very different patients.

Since the electrode holder is itself electrically conductive, when the electrode carrier is put on, said electrode holder, via the shorter leg thereof, comes into contact with the metal sleeve and hence into contact with the stimulation electrode.

The electrode holder is fixed on the nosepiece via the holding pin; from there it can continue to be wired up electrically.

Such electrode holders are likewise provided as replaceable parts and hence as separate economic goods because the electrode holders could, for example, bend out of shape in the case of multiple uses. Furthermore, it may be desirable for hygienic reasons to replace the electrode holders after multiple uses.

The present invention furthermore relates to a device for electrostimulation of the eye, having a spectacles-like frame with a nosepiece, an arrangement, connected to the nosepiece, for holding the frame on the head of a patient and at least one electrode holder, arranged on the nosepiece in adjustable fashion, for holding a stimulation electrode arrangement, with the stimulation electrode arrangement being the novel stimulation electrode arrangement and the novel electrode holder preferably being used as electrode holder.

Here, the nosepiece can have a nose clip and two eye brackets, to which respectively one electrode holder is attached.

Here, the eye brackets furthermore are preferably electrically insulated from one another and contacted individually such that a therapy with different current strengths for the two eyes is possible.

Here, the arrangement for holding the frame has two earpieces which are fixed to the nosepiece, preferably fixed thereto in foldable fashion, in a manner known per se.

In general, it is also preferable for a counter electrode to be provided for the stimulation electrode.

Further advantages emerge from the description of the attached drawing.

It is understood that the aforementioned features and the features yet to be explained below can be used not only in the respectively specified combination but also in other combinations or on their own, without departing from the scope of the present invention.

An embodiment of the invention is illustrated in the drawing and will be explained in more detail in the following description. In which.

Figure 1:
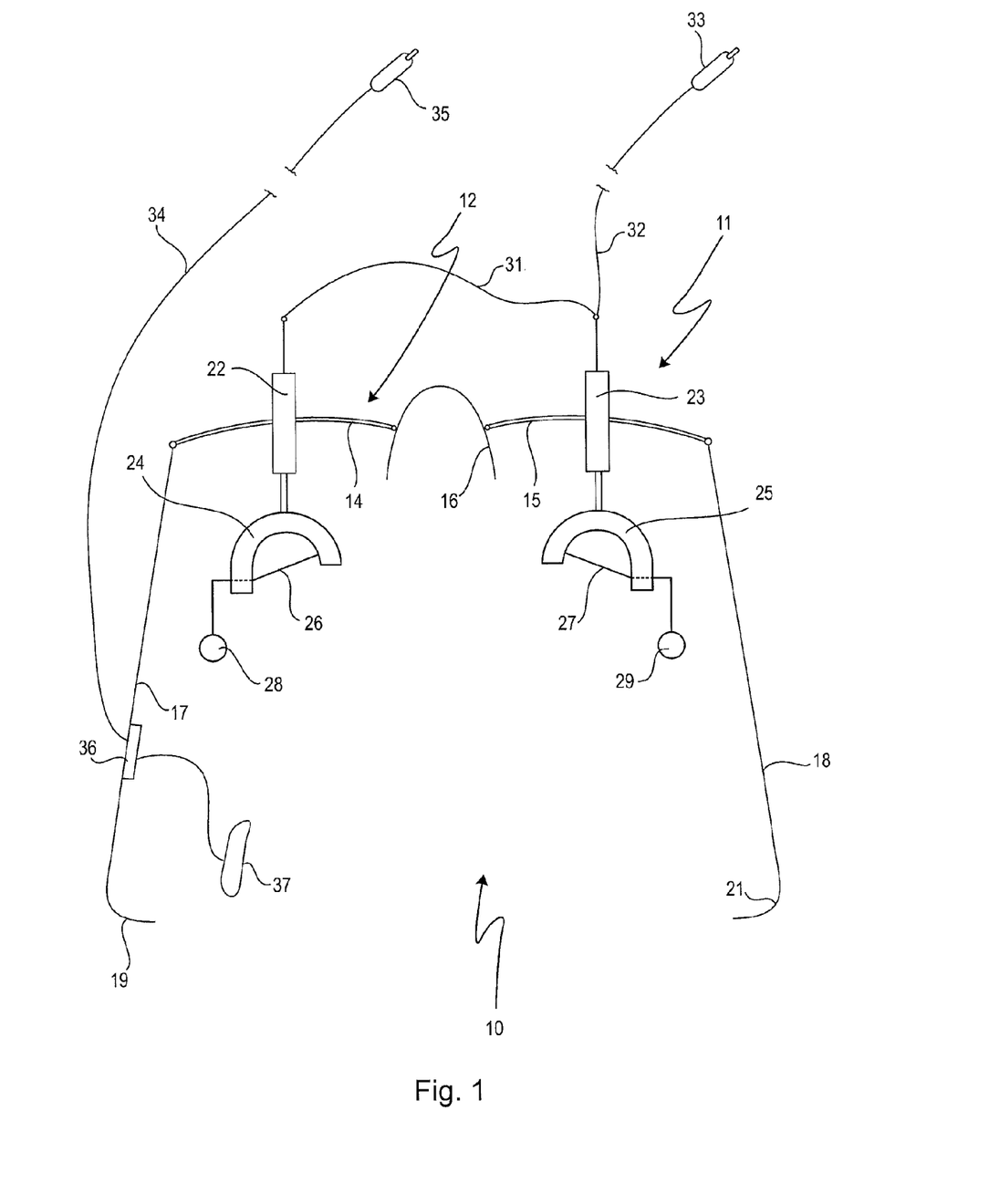
FIG. 1 shows a schematic perspective illustration of the novel device with the novel electrode holder and the novel electrode carrier.

In FIG. 1, at 10 a device is shown which serves for the electrostimulation of the eye. The device 10 comprises a spectacles-like frame 11 which has a nosepiece 12 on which two eye brackets 14, 15 are formed, the latter corresponding to the position of the eye of the patient. The two eye brackets 14 and 15 are interconnected via a nose clip 16.

As is conventional in spectacles, the nosepiece 12 is provided with an arrangement for holding the frame 11 on the head of a patient. This arrangement has two earpieces 17 and 18, which are mounted on the nosepiece 12 in foldable fashion and have a bent-off design at the free ends 19 and 21 thereof such that the frame 11 can be fitted in optimum fashion to the physiognomy of a patient.

Arranged on each eye bracket 14 and 15, which can optionally be slightly curved, there is an adjustment holder 22 and 23, on which respectively one electrode holder 24 and 25, respectively, is attached in adjustable fashion.

The adjustment holders 22 and 23 are merely a schematic representation for the option of attaching the electrode holder 24 and 25, respectively, to the eye bracket 14 and 15, respectively, such that it can be adjusted in all three spatial directions relative to the eye brackets 14 and 15.

This is how it is possible to align the electrode holders 24, 25 in optimum fashion with respect to the eye of the respective patient.

Each electrode holder 24, 25 carries a wire-shaped stimulation electrode 26 and 27, respectively, which is pretensioned via a weight 28 and 29, respectively.

Once this device has been optimally fitted to the physiognomy of a patient, the two stimulation electrodes 27 and 28 come into contact with the cornea of the eye. The stimulation electrodes 26, 27 arc out in the process such that they come to rest fitting the arcing of the cornea. This is possible because the stimulation electrodes 26, 27 are inherently flexible and are clamped in flexible fashion in the U-shaped electrode holder 24 and 25, respectively, via the weights 28 and 29.

As will still be set out below, the stimulation electrodes 26, 27 are electrically conductively connected to the electrode holders 24, 25 such that they can be switched in parallel via a cable 31 which interconnects the two electrode holders 24 and 25.

The cable 31 is connected to a connection cable 32 with a plug 33, which can be inserted into a stimulation instrument (not shown in this application).

A plug 35 of a second connection cable 34 is likewise connected to the stimulation instrument (not shown), with the cable 34 being routed to a holder 36 on the earpiece 17 and from there to a counter electrode 37 which is suitably attached to the forehead of the patient.

Here, provision can be made for the two connection cables 32, 34 to run physically parallel to one another and to be connected to a common multi-way plug, which replaces the two separate plugs 33, 35. This makes it easier for the patient to connect the connection cables 32, 34 to the stimulation instrument (not shown).

As a result of this the electric circuit is, so to speak, closed over the body of the patient.

Any stimulation instrument that can emit suitable pulse-shaped electrical stimulation signals for treating the eye can be used as stimulation instrument to be connected to the plugs 33 and 35.

In respect of further references, reference is made, for example, to WO 2011/086150 A1, mentioned at the outset.

A clinical trial relating to the electrostimulation of the eye was published by e.g. Schatz et al., "Transcorneal Electrical Stimulation for Patients with Retinitis Pigmentosa—a Prospective, Randomized, Sham-Controlled Exploratory Study", in Investigative Ophthalmology & Visual Science (published online on 5 Apr. 2011 as manuscript iovs. 10-6932).

Figure 2:
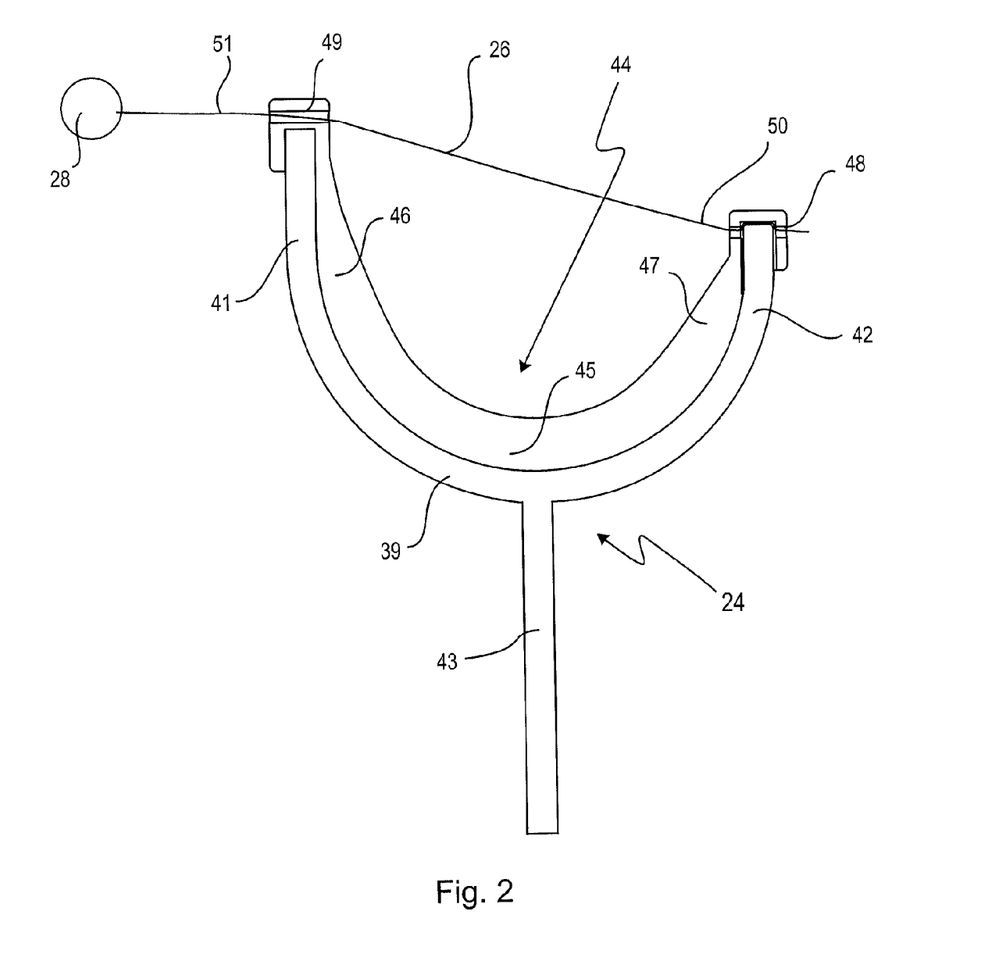
FIG. 2 shows an enlarged, partially sectioned schematic illustration of the electrode holder from FIG. 1.

FIG. 2 shows an enlarged cross section of the electrode holder 24 from FIG. 1, with the upper ends being sectioned.

First of all, it is possible to identify that the electrode holder 24 has a U-shaped wire body 39 with a longer leg 41 and a shorter leg 42. Provided on the U-shaped wire body 39 and pointing away from the legs 41, 42 is a holding pin 43, which can be inserted into the adjustment holders 22, 23 in order to attach the electrode holder 24 on the frame 11 from FIG. 1.

An electrode carrier 44, which comprises a U-shaped bracket with a longer first arm 46 and a shorter second arm 47, is inserted into this U-shaped wire body 39.

A passage opening 48 is provided in the shorter arm 47 and a passage opening 49 is provided in the longer arm 46. Running through these passage openings 48 and 49 is the wire-shaped stimulation electrode 26, which, with the first end 50 thereof, is fixed or electrically contacted in the passage opening 48.

With the second end 51 thereof, the stimulation electrode 26 runs through the passage opening 49 and then ends in the weight 28.

The weight 28 tightly tensions the stimulation electrode 26 between the two arms 46 and 47, although, as a result of the low mass of the weight 28 (1 to 20 g are preferred), the latter can be slightly bent inwards when it is placed against the cornea of an eye.

Together with the weights 28, 29, the respective electrode carrier 44 and the respective stimulation electrode 26, 27 are combined in non-detachable fashion to form a stimulation electrode arrangement, which can be attached to the electrode holders 24, 25 in a replaceable fashion.

It is possible to identify in FIG. 2 that the electrode carrier 44 cannot be inserted into the electrode holder 24 when the former has been rotated by 180° because the shorter arm 47 would then come to rest on the longer leg 41, and so the U-shaped bracket 45 cannot rest completely against the U-shaped wire body 39.

Visually impaired or blind patients can therefore also identify and correct an incorrect alignment when inserting the stimulation electrode 26 provided with the electrode carrier 44.

As is possible to identify also from FIG. 1, the electrode holders 24, 25 are attached to the spectacles-like frame 11 such that the shorter legs 42 thereof are arranged on the nose side and the longer legs 41 thereof are on the temple side, i.e. there where the weights 28 and 29 also hang down from.

Figure 3:
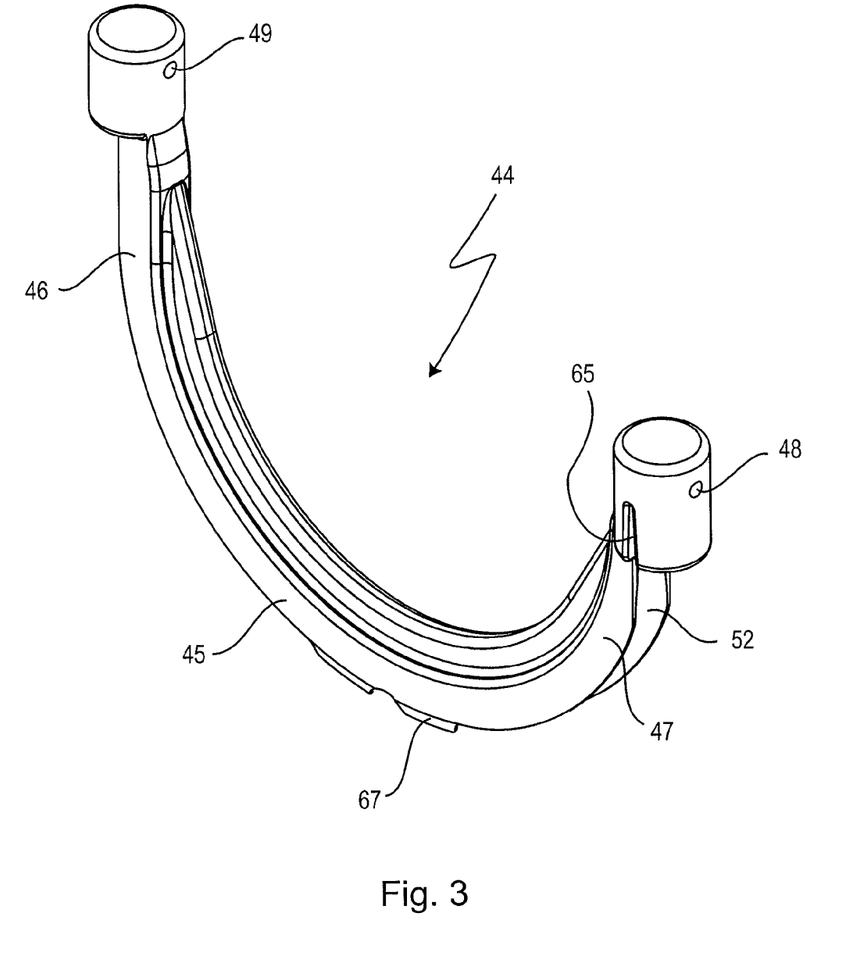
FIG. 3 shows a perspective illustration of the electrode carrier which can be inserted into the electrode holder from FIG. 1.

FIG. 3 shows the electrode carrier 44 from FIG. 2 in a perspective illustration.

The electrode carrier 44 has a groove 52, which extends along the curved body 45 of the former, is open towards the outside and latched onto the U-shaped wire body 39 if electrode carrier 44 and electrode holder 24 are put together with the correct alignment with respect to one another. The groove 52 furthermore serves as guide rail.

Furthermore, it is possible to identify a latching projection 67, which allows the electrode carrier 44 to latch into the electrode holder 24. The latching projection 67 thus prevents the electrode carrier 44 from inadvertently detaching from the electrode holder 24.

Figure 4:
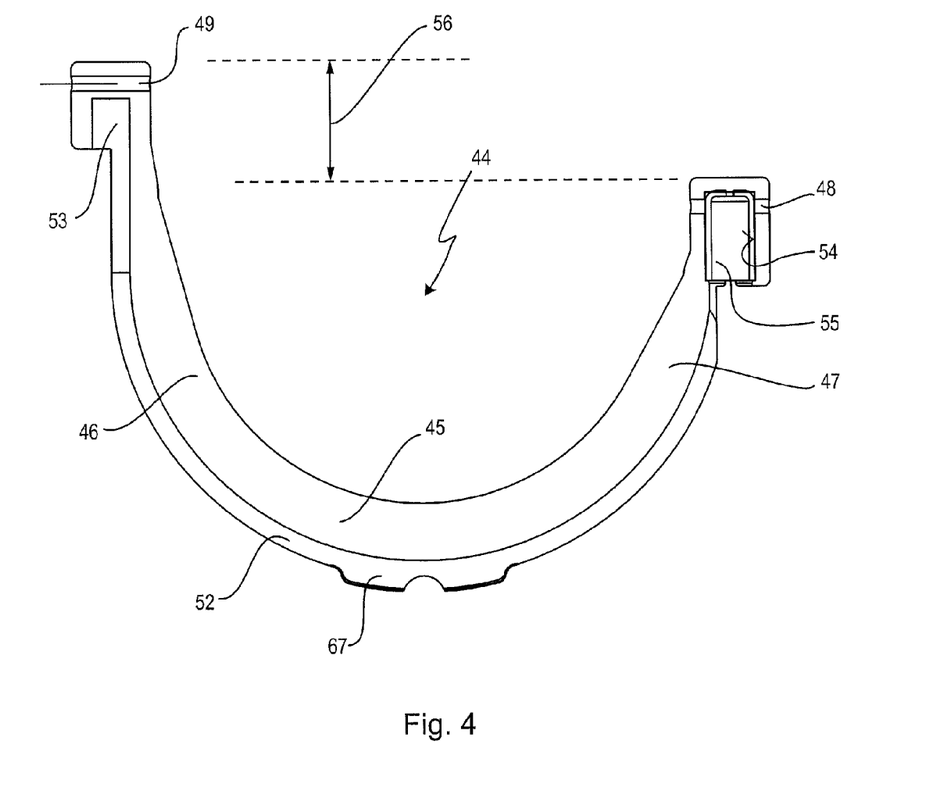
FIG. 4 shows a partially sectioned cross section through the electrode carrier from FIG. 3.

FIG. 4 shows a longitudinal section through the electrode holder 44 from FIG. 3, sectioned at the upper ends of legs 41, 42.

Thickenings with blind-hole bores 53 and 54 are respectively arranged on the outer free ends of the arms 46 and 47, with the blind-hole bore 53 running perpendicular to the passage bore 49 but not intersecting the latter.

In contrast thereto, the blind-hole bore 54 likewise runs perpendicular to the passage bore 48 but is intersected by the latter.

Situated in the blind-hole bore 54 there is a metal sleeve 55 which, as will still be explained below, serves to fix the stimulation electrode mechanically and to contact the latter electrically.

It is also possible to identify from FIG. 4 that the longer first arm 46 is longer than the second arm 47 by an amount 56.

Depending on the physiognomy of the patient, the amount 56 is between 4 and 20 mm, with the difference in length 56 preferably corresponding to approximately 8 mm.

Figure 5:
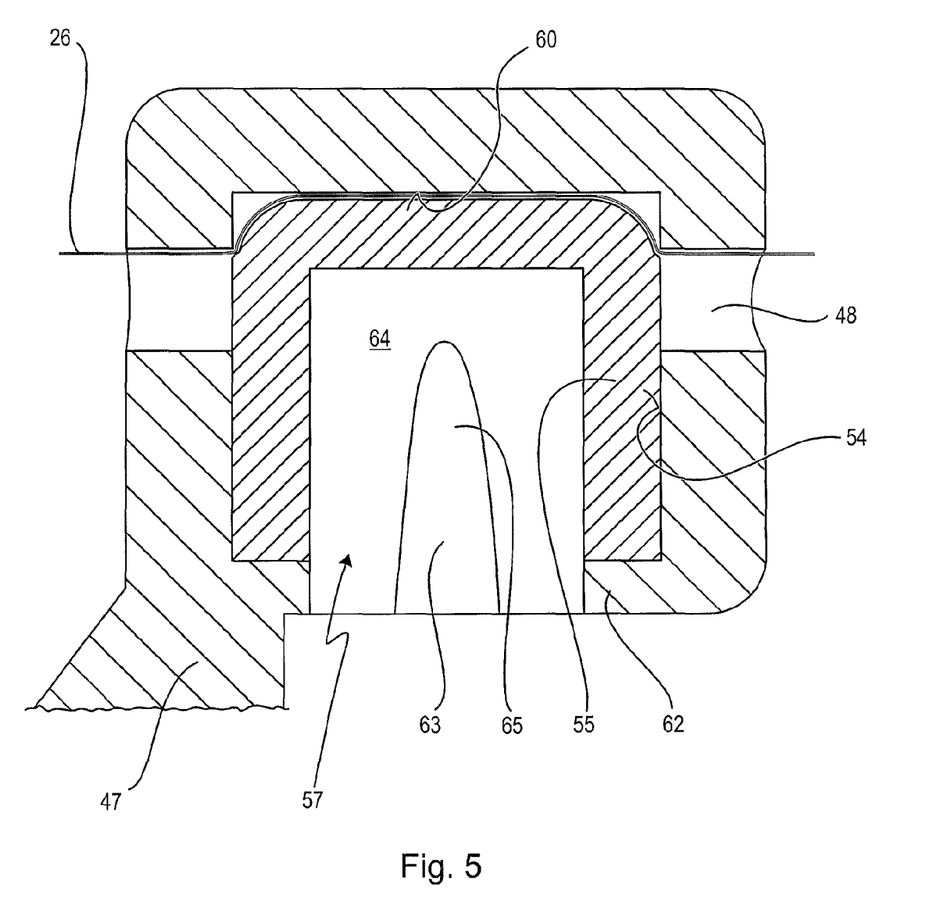
FIG. 5 shows a sectioned enlarged illustration of the electrode carrier from FIG. 4 at the upper end of its shorter arm.

FIG. 5 shows the upper end of the shorter arm 47 with the blind-hole bore 54 in a greatly enlarged sectioned illustration.

It is possible to identify that the blind-hole bore 54 with the metal sleeve 55 contained therein forms a type of plug-in contact 57. If the free end of the leg 42 of the electrode carrier 24 is inserted into the metal sleeve 55, an electrical contact is established at the same time between metal sleeve 55 and electrode holder 24.

Here, the metal sleeve presses the wire-shaped stimulation electrode extending through the passage bore 48 against an end wall 60 of the passage bore 48.

The metal sleeve 55 is held in the passage bore 48 by a collar 62, which extends inwardly into the blind-hole bore 54 and surrounds an opening 63 through which the leg 42 can be inserted.

So that the metal sleeve 55 can be inserted into the blind-hole bore 54 while the collar 62 widens, a longitudinal slit 65, which can also be identified in FIG. 3, is provided in the wall 64 of the blind-hole bore.

If the metal sleeve 55 is now pushed into the opening 53, the collar 62 widens and then springs back again, and so the metal sleeve 55 is held in a non-detachable fashion and is, simultaneously, pressed against the wall 60, where it securely clamps the stimulation electrode.

The invention claimed is:

1. A stimulation electrode arrangement to be used in a device for electrostimulation of an eye of a patient,
the device comprising a spectacles-like frame provided with a nosepiece, a holding arrangement for holding the frame on the head of the patient, and at least one electrode holder for holding a wire-shaped stimulation electrode, said electrode holder being arranged on the nosepiece in an adjustable fashion, and said holding arrangement being connected to the nosepiece,
the stimulation electrode arrangement comprising an electrode carrier, said electrode carrier being attachable to said electrode holder in a detachable fashion, and said stimulation electrode being arranged on said electrode carrier,
wherein the stimulation electrode comprises a first end, said first end connected to the electrode carrier in an electrically conductive fashion, and
wherein the electrode carrier comprises at least one passage opening and said stimulation electrode comprises a second end, the stimulation electrode being routed through said at least one passage opening and being provided with a weight at its second end.

2. The stimulation electrode arrangement of claim 1, wherein the electrode carrier is a U-shaped bracket having a first and a second arm, a first passage opening being provided on said first arm and a second passage opening being provided on second arm, said stimulation electrode running through said first and second opening, said plug-in contact being arranged on the second arm.

3. The stimulation electrode arrangement of claim 2, wherein the first arm is longer than the second arm.

4. The stimulation electrode arrangement of claim 3, wherein the first arm is at least 4 mm longer than the second arm.

5. The stimulation electrode arrangement of claim 2, wherein on said U-shaped bracket an outwardly open groove is provided for receiving said electrode holder, said electrode holder having a wire body fitting into said groove.

6. The stimulation electrode arrangement of claim 5, wherein said wire body comprises a first and a second leg, said first arm of said U-shaped bracket comprises a first blind-hole bore running approximately perpendicular to said first passage opening, said second arm of said U-shaped bracket comprises a second blind-hole bore running approximately perpendicular to said second passage opening, said first blind-hole bore for holding said first leg and said second blind-hole bore for holding said second leg.

7. The stimulation electrode arrangement of claim 6, wherein the second passage opening in the second arm extends through the second blind-hole bore, a metal sleeve being situated in said second blind-hole bore, which metal sleeve mechanically fixes said first end of said stimulation electrode in said second passage opening and serves as plug-in contact for holding and electrically contacting said second leg of the wire body.

8. The stimulation electrode arrangement of claim 7, wherein said second blind-hole bore in said second arm is provided with an opening, a wall, a longitudinal slit in said wall, and a collar surrounding said opening.

9. The stimulation electrode arrangement of claim 1, wherein the electrode carrier is an injection-moulded part.

10. The stimulation electrode arrangement of claim 1, wherein the stimulation electrode is a DTL-like electrode.

11. The stimulation electrode arrangement of claim 1, wherein the stimulation electrode comprises a wire selected from the group consisting of a noble metal wire, a special steel alloy wire, and a polymer thread with a metallic coating.

12. The stimulation electrode arrangement of claim 1, wherein the electrode carrier is provided with an electrical plug-in contact for contacting the electrode holder, the first end of the stimulation electrode being electrically connected to the plug-in contact.

13. The stimulation electrode arrangement of claim 5, wherein the wire body is U-shaped.

14. The stimulation electrode arrangement of claim 1, wherein the electrode holder is made of electrically conductive material.

15. The stimulation electrode arrangement of claim 1, wherein the electrode holder comprises a wire body for plugging on the electrode carrier and a holding pin for attachment to the nosepiece.

16. The stimulation electrode arrangement of claim 1, wherein the nosepiece comprises a nose clip and a first and a second eye bracket, a first electrode holder being attachable to said first eye bracket and a second electrode holder being attachable to said second eye bracket.

17. The stimulation electrode arrangement of claim 1, wherein said holding arrangement comprises two earpieces fixed to the nosepiece.

18. The stimulation electrode arrangement of claim 1, further comprising a counter electrode for the stimulation electrode.

* * * * *